US008814847B2

(12) United States Patent
Hoffman et al.

(10) Patent No.: US 8,814,847 B2
(45) Date of Patent: Aug. 26, 2014

(54) DELIVERY SYSTEM FOR PERCUTANEOUS PLACEMENT OF A MEDICAL DEVICE AND METHOD OF USE THEREOF

(75) Inventors: Grant T. Hoffman, Bloomington, IN (US); F. Kristen Bailey, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1226 days.

(21) Appl. No.: 11/827,848

(22) Filed: Jul. 13, 2007

(65) Prior Publication Data
US 2009/0018529 A1  Jan. 15, 2009

(51) Int. Cl.
*A61M 25/00* (2006.01)
*A61F 2/966* (2013.01)
*A61F 2/95* (2013.01)

(52) U.S. Cl.
CPC ............ *A61F 2/966* (2013.01); *A61M 25/0067* (2013.01); *A61M 25/0068* (2013.01); *A61M 2025/0079* (2013.01); *A61M 25/007* (2013.01); *A61M 2205/32* (2013.01); *A61M 2025/0006* (2013.01); *A61F 2/95* (2013.01)
USPC ........... 604/523; 604/264; 604/272; 604/533; 606/108; 606/194; 623/1.11; 623/1.12

(58) Field of Classification Search
CPC ............. A61M 2025/0004; A61M 2025/0006; A61M 2025/0018; A61M 25/0067; A61M 25/0068; A61M 2025/0079; A61M 25/007
USPC ................ 606/108, 109, 194; 623/1.11, 1.12; 604/264, 272, 523, 533
See application file for complete search history.

(56) References Cited

U.S. PATENT DOCUMENTS

| 4,439,197 | A |   | 3/1984 | Honda et al. |
| 4,494,531 | A |   | 1/1985 | Gianturco |
| 4,665,918 | A |   | 5/1987 | Garza et al. |
| 5,324,304 | A |   | 6/1994 | Rasmussen |
| 5,329,942 | A |   | 7/1994 | Gunther et al. |
| 5,387,235 | A | * | 2/1995 | Chuter ......................... 623/1.11 |
| 5,453,090 | A |   | 9/1995 | Martinez et al. |
| 5,591,227 | A |   | 1/1997 | Dinh et al. |
| 5,700,269 | A |   | 12/1997 | Pinchuk et al. |
| 5,984,964 | A | * | 11/1999 | Roberts et al. ............... 623/1.11 |
| 6,129,756 | A | * | 10/2000 | Kugler et al. ................ 623/1.27 |
| 6,200,336 | B1 |   | 3/2001 | Pavcnik et al. |
| 6,478,790 | B2 |   | 11/2002 | Bardani |
| 6,605,109 | B2 |   | 8/2003 | Fiedler |

(Continued)

*Primary Examiner* — Quynh-Nhu H Vu
*Assistant Examiner* — Larry R Wilson
(74) *Attorney, Agent, or Firm* — Brinks Gilson & Lione (57) ABSTRACT

A delivery system for implanting a medical device into the body of a patient or subject and a method of use thereof. The delivery system includes a delivery catheter having a catheter lumen and an inner member extending therethrough. The inner member includes a distal tip portion, a proximal portion, and an intermediate portion, the intermediate portion being disposed adjacent to the distal end of the delivery catheter. A first sealing member, positioned near a distal end of the proximal portion, forms a fluid seal between the inner member and an inside surface of the delivery catheter. A second sealing member, positioned near a proximal end of the distal tip portion, forms a fluid seal between the inner member and an inside surface of the delivery catheter. The intermediate portion extends between the first seal and the second seal. In one embodiment, a medical device and a hydrating fluid are present in a device-containing region between the intermediate portion and the delivery catheter.

15 Claims, 7 Drawing Sheets

(56) References Cited

U.S. PATENT DOCUMENTS

| | | |
|---|---|---|
| 6,835,194 B2 | 12/2004 | Johnson et al. |
| 6,893,431 B2 | 5/2005 | Naimark et al. |
| 2001/0039450 A1 | 11/2001 | Pavcnik et al. |
| 2003/0144670 A1* | 7/2003 | Pavcnik et al. ............... 606/108 |
| 2003/0144970 A1* | 7/2003 | Coyne .......................... 705/400 |

* cited by examiner

Fig. 8 though the side port.
DELIVERY SYSTEM FOR PERCUTANEOUS PLACEMENT OF A MEDICAL DEVICE AND METHOD OF USE THEREOF

FIELD OF THE INVENTION

This invention relates to medical devices and in particular to a system for delivering an implantable medical device to a selected site within a human or veterinary body.

BACKGROUND

Delivery systems have been known for many years and have been used with the Seldinger technique and related percutaneous entry techniques for delivery of implantable medical devices into the vasculature of human or veterinary patients. Such systems typically utilize a wire guide inserted into the vasculature to extend to the site of implantation of a medical device such as a stent, stent graft, filter, occluder, valve or the like. An introducer sheath is placed over a portion of the guide wire, and a catheter inserted over the guide wire within the introducer sheath and beyond its distal tip. The medical device is contained within a distal portion of the catheter until delivery to the site of implantation. The medical device is then released from the catheter distal tip and deployed. The insertion and delivery procedure are monitored closely through fluoroscopy, angiograms or CT scanning or the like. Radiopaque markers are commonly used as landmarks on the wire guide, catheter and medical device to assure eventual accurate positioning of the device at the site of implantation and its full deployment.

One delivery system is known from U.S. Pat. No. 4,494,531 for delivery of a vena cava filter into the vena cava of the vasculature. The system includes a wire guide with a handle and a catheter that contains the filter at its distal end in a reduced diameter confinement. Once access is gained to the vasculature by an introducer sheath and a dilator, and the dilator is removed from the sheath, the catheter is inserted through the sheath until its distal end reaches the deployment site. The collapsed filter is then deployed by gradually retracting the catheter's distal end, while the filter is held axially fixed by a positioning wire guide extending to the proximal end of the filter. This process initially exposes the distal end of the filter, which includes outwardly curving struts with barbs. The exposed filter then expands so that its distal barbs engage and seat in the vessel wall in cooperation with sharp, forward jabs or manipulation of the catheter. The remainder of the filter then forms a "bird's nest" and its proximal barbs engage and seat in the vessel wall to anchor the filter in position as the catheter continues to be retracted. The particular filter disclosed in the patent is sold by Cook Incorporated, Bloomington, Ind. as the Gianturco-Roehm BIRD'S NEST Vena Cava Filter. Other delivery systems for filters are disclosed in U.S. Pat. Nos. 5,329,942 and 5,324,304.

U.S. Patent Publication No. 2003/0144670A1, published Jul. 31, 2001, discloses a delivery system, for medical devices such as vascular valves, that provides for assuredly centering the distal ends of the device during deployment from the delivery catheter and allows precise visualization of radiopaque markers on the device being implanted. This delivery system also enables hydration of any lyophilized tissue contained within the medical device at the time of delivery into the patient.

SUMMARY

The present invention provides a delivery system for implanting a medical device into the vessel of a human or veterinary patient and methods of use thereof. In one embodiment, the delivery system includes a delivery catheter having a catheter lumen extending through the delivery catheter and an inner member extending through the catheter lumen from the proximal end to the distal end of the delivery catheter. The inner member includes a distal tip portion, a proximal portion and an intermediate portion. The intermediate portion is disposed adjacent to the distal end of the delivery catheter. An inner lumen extends longitudinally through the inner member from the proximal end to the distal end.

The delivery system also includes a first sealing member positioned between the inner member and the delivery catheter and forming a fluid seal between the inner member and an inside surface of the delivery catheter. A second sealing member is positioned distally from the first sealing member between the inner member and the delivery catheter and also forms a fluid seal between the inner member and an inside surface of the delivery catheter. The intermediate portion is at least that portion extending between the first sealing member and the second sealing member. A device-containing region is contained between the intermediate portion and the delivery catheter and between the first sealing member and the second sealing member.

In one embodiment, the intermediate portion is sized and shaped to engage an implantable medical device between the inner member and the delivery catheter. In another embodiment, an implantable medical device is positioned within the device-containing region. A hydrating fluid can also be contained within the device-containing region.

In yet another embodiment, the inner member includes a delivery lumen extending longitudinally therethrough from a lateral port near the proximal end of the inner member to the device-containing region.

In another embodiment, the delivery catheter includes a side port providing fluid communication between the device-containing region and the outside of the catheter when the side port is positioned proximally of the second sealing member and distally of the first sealing member. In yet another embodiment, the delivery catheter includes a plurality of side ports.

In one embodiment, at least one of the sealing members is a ring seal. In another embodiment, at least one of the sealing members is an O ring seal.

In another embodiment, the implantable medical device is an expandable medical device requiring or benefiting from maintenance of hydration of at least part of the implantable medical device.

In one embodiment, the inner member includes a radiolucent material. In another embodiment, the delivery catheter includes a radiopaque material.

Another aspect of the present invention provides a method for delivering an implantable medical device to a body vessel. The method includes providing the delivery system of the invention having the side port positioned distally of the second sealing member, so as to isolate the device-containing region from the exterior of the device. The device containing region contains the implantable medical device and a hydrating fluid.

The side port proximally is positioned of the second sealing member and distally of the first sealing member to provide a fluid communication path between the device-containing region and an exterior of the delivery catheter. A flushing fluid is delivered to the device-containing region via the delivery lumen, so as to expel at least a portion of the hydrating fluid though the side port.

The device-containing region is positioned at the required delivery position within the body vessel and the device-containing region positioned beyond the distal end of the delivery catheter. The implantable medical device is deployed and the delivery system withdrawn from the body vessel.

In one embodiment, the implantable medical device is an expandable medical device requiring or benefiting from maintenance of hydration of at least part of the implantable medical device.

In another embodiment, the method also includes delivering a distal portion of a guide wire to the delivery site within the body vessel and positioning the proximal end of the guide wire within the inner lumen at the distal end of the inner member. The device-containing region is delivered via a path defined by the guide wire.

In one embodiment, the method delivers a self-expendable medical device. In another embodiment, the method delivers a venous valve.

Another aspect of the invention provides a kit including the delivery system of the invention, an implantable medical device positioned in a device-containing region of the delivery system and a hydration fluid contained in the device-containing region and in contact with at least a portion of the implantable medical device.

BRIEF DESCRIPTION OF THE DRAWINGS

Embodiments of the delivery systems and methods of the present invention will now be described by way of example with reference to the accompanying drawings, in which:

FIGS. 8(a)-(c) depict cross sectional views of ring seals suitable for use with the delivery system of the invention.

DEFINITIONS

Unless otherwise defined, all technical and scientific terms used herein have the same meaning as commonly understood by one of ordinary skill in the art to which this invention pertains. In case of conflict, the present document, including definitions, will control.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "implantable" refers to an ability of a medical device to be positioned at a location within a human or veterinary body, such as within a body vessel. Furthermore, the terms "implantation" and "implanted" refer to the positioning of a medical device at a location within the body, such as within a body vessel.

The terms "proximal" and "distal" are used to denote a direction or position relative to each other. Unless otherwise indicated, the recitation of "proximal" or "distal" portions of a device does not refer to any particular orientation of the device within a body.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

One aspect of the present invention provides a delivery system useful for the percutaneous delivery of an implantable medical device to a body lumen. The delivery system is particularly applicable to the delivery of an implantable medical device having at least one component requiring or benefiting from the maintenance of a hydrated environment. Examples of such medical devices include, but are not limited to, grafts, stent grafts, vena cava filters, valves such as heart valves or venous valves, and a variety of other devices having a natural tissue or synthetic polymer component.

In one embodiment, the implantable medical device is a venous valve, such as the type disclosed in U.S. Pat. No. 6,200,336 or U.S. Publication No. 2001/0039450A1, published Nov. 8, 2001, the contents of which are incorporated herein by reference. The stent valve disclosed therein includes a "square" stent frame having extracellular matrix material, such as small intestine submucosa (SIS) material, secured thereto and extending between the frame struts and having a valve opening or slit through the material. Such a valve stent is deliverable to a treatment site in the vasculature and is deployable without any specific control device within the delivery catheter. The valve stent self-expands and self-seats in position in the vessel as the catheter distal end is retracted. Certain such valve stent devices may require the device to be maintained in a hydrated state prior to and during delivery.

Figure 1:
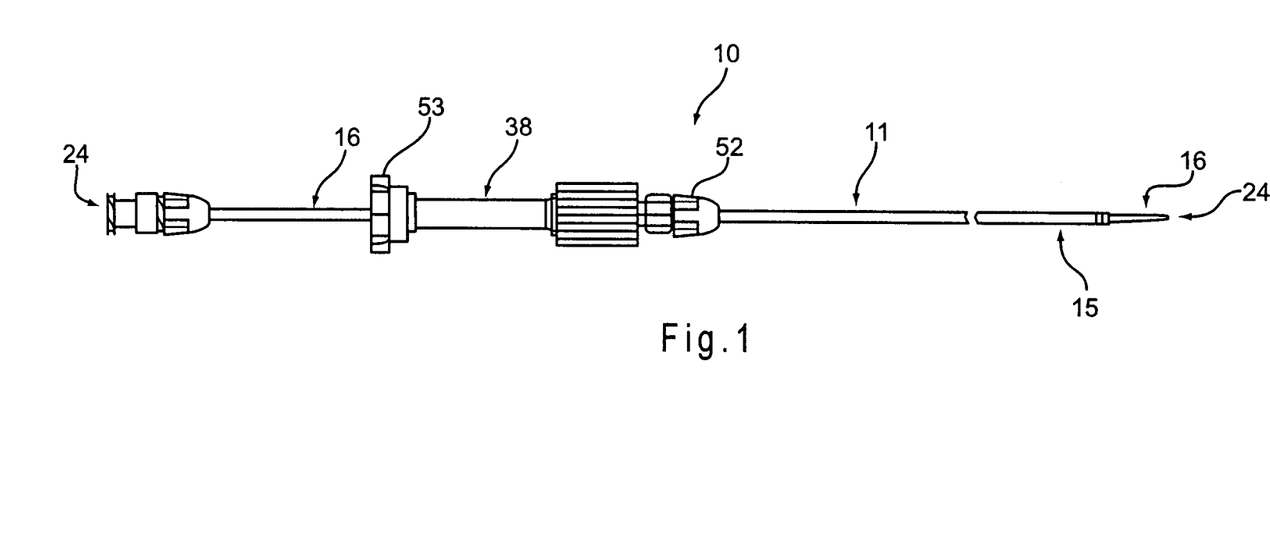
FIG. 1 depicts a top view of an embodiment of the delivery system of the invention.

FIG. 1 depicts a top view of one embodiment of the delivery system 10 of the invention. The delivery system includes delivery catheter 11 having a catheter lumen through which inner member 16 is inserted therethrough. Device-containing region 15 is contained between delivery catheter 11 and inner member 16 near the distal end of the device. Well-known Luer-lock connecter hub 52 is affixed to the proximal end of the delivery catheter. A connector 38 is connected to connector hub 52 of the delivery catheter through which inner member 16 is also inserted and extended therethrough. Threaded lock 53 at the proximal end of connector 38 is rotated to fixedly position inner member 16 longitudinally with respect to the delivery catheter and the connector.

A medical device contained in the delivery system of the invention is typically delivered percutaneously to a vascular deployment site over a well-known wire guide that is inserted into the vascular system and to the deployment site. Inner lumen 24 extends longitudinally through inner member 16 as well as the delivery system, which is introduced over the wire guide through inner lumen 24. Of course, the devices of the invention have applications for the delivery of medical devices to other deployment sites within the body.

Figure 2:
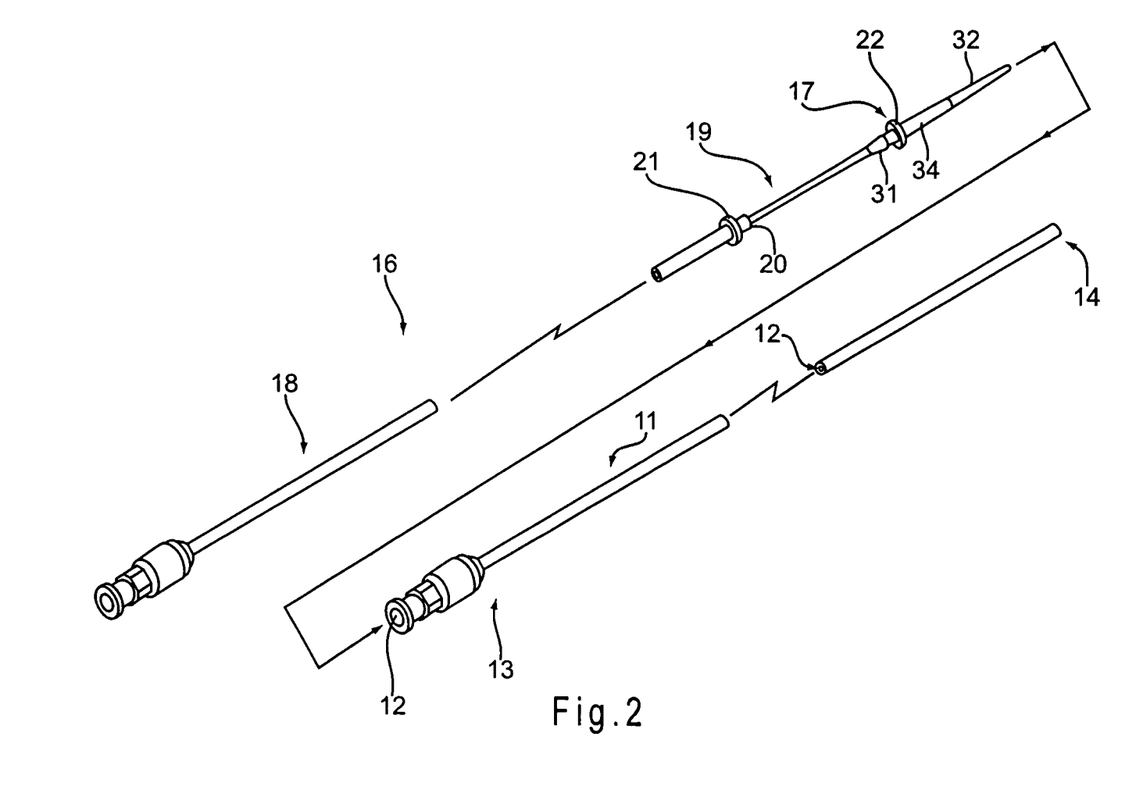
FIG. 2 depicts an exploded and enlarged view of the delivery catheter and the inner member of the delivery system of FIG. 1.

FIG. 2 depicts an exploded and enlarged view of delivery catheter 11 and inner member 16 of delivery system 10 of FIG. 1. Inner member 16 is insertable through catheter lumen 12 of delivery catheter 11 that extends longitudinally between proximal end 13 and distal end 14. Inner member 16 includes a distal tip portion 17, proximal portion 18 and intermediate portion 19 disposed between distal tip portion 17 and proximal portion 18.

A first sealing member 21 is positioned around inner member 16 near the distal end of proximal portion 18 such that, when inner member 16 is positioned within catheter lumen 12 of delivery catheter 11, first sealing member 21 forms a fluid seal between inner member 16 and the inside surface of delivery catheter 11. A second sealing member 22 is positioned around inner member 16 near the proximal end of distal tip portion 17 such that, when inner member 16 is positioned within catheter lumen 12, second sealing member 22 forms a fluid seal between inner member 16 and the inside surface of delivery catheter 11.

Figure 8:
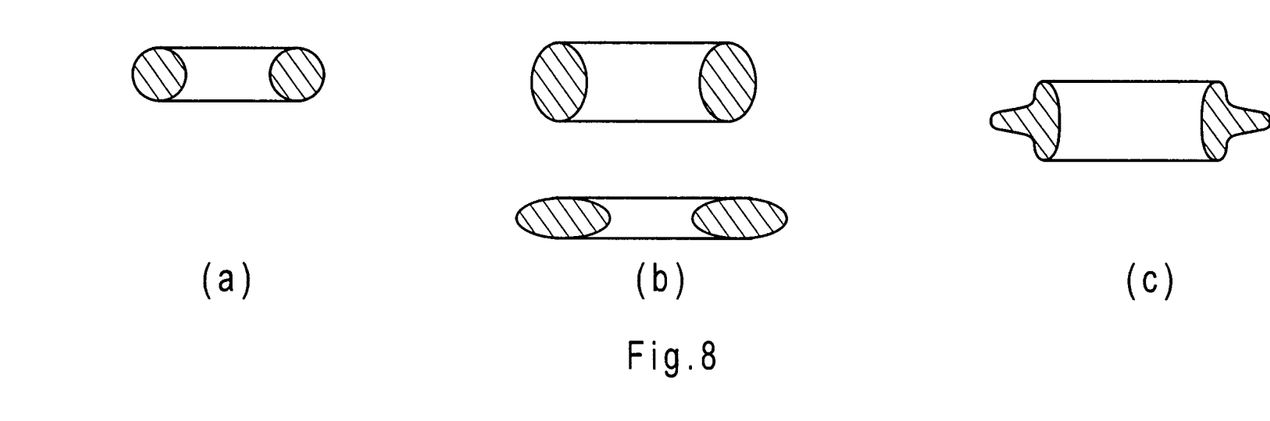
FIG. 8(a) depicts a ring seal having a circular cross section.
FIG. 8(b) depicts two embodiments of a ring seal having an elliptical cross section.
FIG. 8(c) depicts a ring seal having a T shaped cross section.

In one embodiment, the sealing member is a ring seal. The ring seal can have a cylindrical cross section, i.e. an O ring seal. Alternatively, the ring seal can have an elliptical or T shaped cross section. FIGS. 8(a)-(c) depict cross sectional views of examples of ring seals suitable for use with devices of the invention. FIG. 8(a) depicts a ring seal having a circular cross section. FIG. 8(b) depicts two embodiments of ring seals having an elliptical cross section. FIG. 8(c) depicts a ring seal having a T shaped cross section.

In one embodiment, intermediate portion 19 extends between first sealing member 21 and second sealing member 22 and is sized and shaped to provide a device-containing region between intermediate portion 19 and the inside surface of delivery catheter 11. Typically, at least a portion of intermediate portion 19 has a reduced radial size compared to proximal portion 18 and the maximum radial size of distal tip portion 17. The presence of the sealing members allows for the isolation of the device-containing region from the external environment of the delivery device and, in one embodiment, allows for the maintenance of a hydrating environment within the device-containing region by including a hydrating fluid within the device-containing region. In other embodiments, second sealing member 22 is positioned towards the center of, or near or at the proximal end of, proximal portion 18. In such embodiments, a hydrating environment can be maintained within a larger portion of the device between the interior of delivery catheter 11 and inner member 16.

A medical device such as the aforementioned stent valve may be positioned around intermediate portion 19 of inner member 16 and contained in a compressed state within the device-containing region. In a particular embodiment, the medical device is a stent valve including lyophilized tissue material that is affixed to a collapsible wire stent frame. The lyophilized tissue material has a slit therein through which intermediate portion 19 of inner member 16 is inserted and engages the tissue material when the stent valve is positioned around intermediate portion 19. The stent valve is maintained in a compressed state by delivery catheter 11 when inner member 16 and the stent valve are inserted therein.

The assembled medical device delivery system 10 has inner member 16 extending through catheter lumen 12 and beyond the distal end of delivery catheter 11. The compressed medical device is contained in the device-containing region of the delivery catheter adjacent distal end 14 of the delivery catheter. The compressed stent valve may be deployed at the desired vascular site by maintaining inner member 16 in a stationary position and withdrawing or pulling back delivery catheter 11 from intermediate portion 19 of inner member 16.

In one embodiment, device-containing region 19 also contains a fluid that provides a hydrating environment within the device-containing region. Suitable hydrating fluids include, but are not limited to, sterilized water, saline or phosphate buffered saline. However any fluid that is compatible with the material of the medial device and with delivery to a body lumen can be used. The presence of first and second sealing members 21 and 22 maintains the hydrating fluid within the device-containing region so that the medical device is maintained in a hydrated state.

Figure 3:
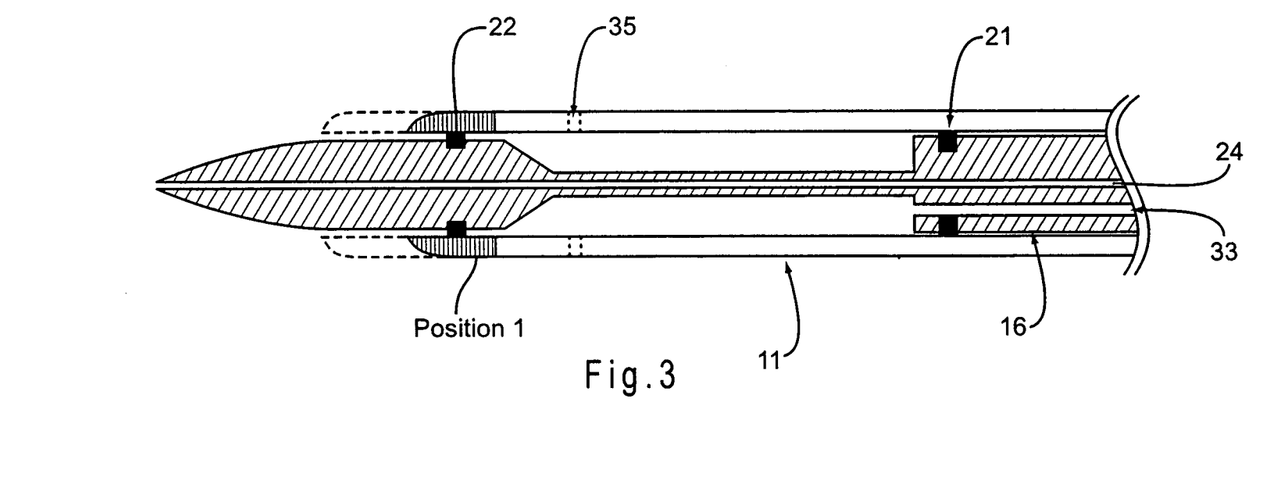
FIG. 3 depicts an enlarged view of one embodiment of the distal portion of the delivery catheter and the inner member.

FIG. 3 depicts an enlarged view of the distal portions of delivery catheter 11 and inner member 16 of another embodiment of the invention. In this embodiment, first and second sealing members 21 and 22 define the device-containing region. Inner lumen 24 extends longitudinally through inner member 16 and can accommodate a wire guide over which the medical device may be delivered. Delivery lumen 33 extends from near the proximal end of inner member 16 to the device-containing region. Delivery catheter 11 contains at least one side port 35. Certain embodiments include a plurality of side ports 35. Delivery lumen 33 may contain at least one isolation valve (not illustrated) that can be used to close the fluid path from the device-containing region to the exterior of the delivery system. For example, the isolation valve may be positioned at or near the proximal end of inner member 16.

Figure 4:
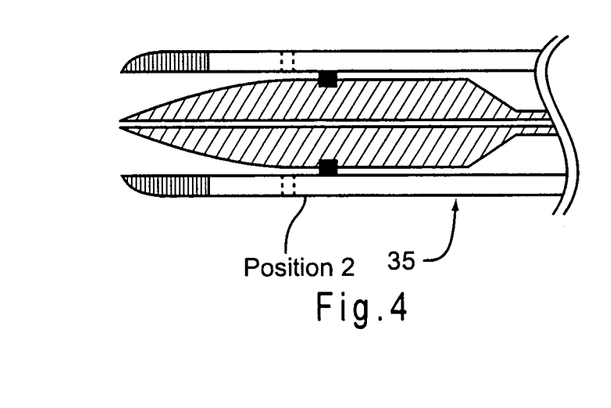
FIG. 4 depicts an enlarged view of one embodiment of a portion of the distal portion of the delivery catheter and the inner member.

When the relative positions of delivery catheter 11 and inner member 16 are such that side port 35 is positioned proximally of second sealing member 22 and distally of first sealing member 21 (Position 1—illustrated in FIG. 3), side port 35 provides a fluid communication path between the inside of the device-containing region and the outside of the delivery system. Such a positioning is illustrated in FIG. 3. When delivery catheter 11 and inner member 16 are positioned so that side port 35 is positioned distally of second sealing member 22 (Position 2—illustrated in FIGS. 3 and 4), the device-containing region is not in fluid contact with the outside of the delivery system.

Figure 5:
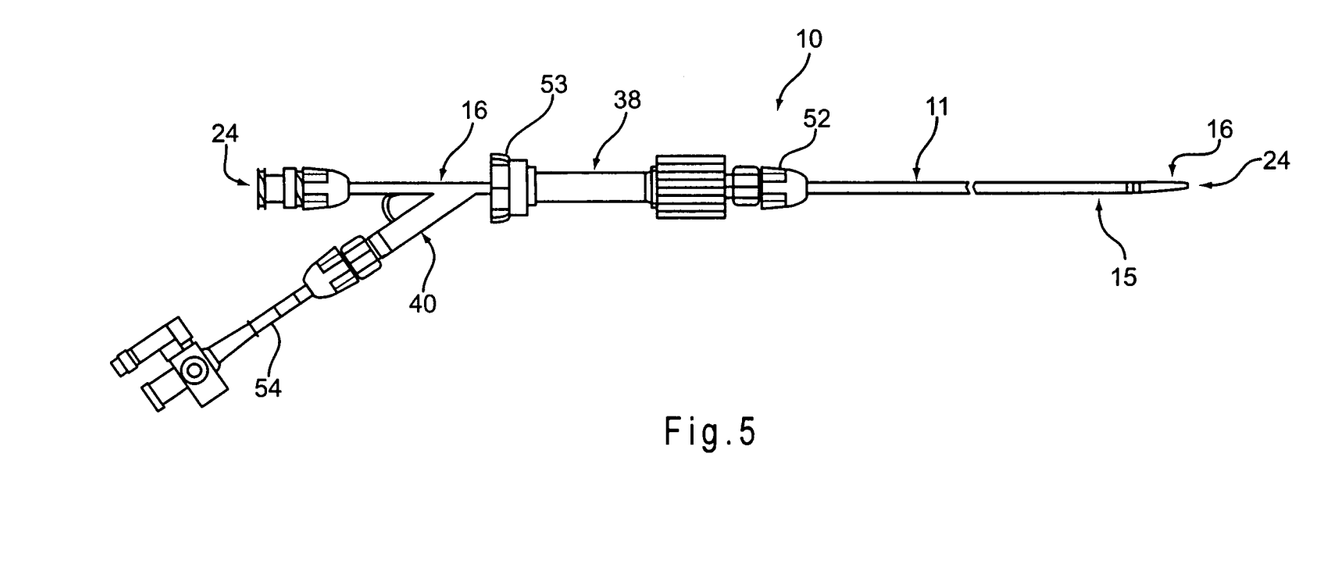
FIG. 5 depicts a top view of an another embodiment of the delivery system of the invention.

In one embodiment, the delivery system includes a delivery port in fluid communication with the proximal end of delivery lumen 33. FIG. 5 illustrates such an embodiment. Side arm 40 of a Y-connector extends laterally at an acute angle proximally from near the proximal end of inner member 16. A fluid irrigation source (not shown) is connected to side arm 40 via well-known inner interconnecting tubing and valve 54. The side arm of the Y-adaptor or connector permits the delivery of a fluid to device-containing region 15 via delivery lumen 33.

Referring again to FIG. 2. An advantage of the present invention is that reduced diameter intermediate portion 19 of inner member 16 is inserted through and engages the medical device for centering the medical device in the vessel in which the device is being deployed. To maintain the longitudinal position of the medical device in the vessel during deployment, proximal portion 18 of inner member 16 includes a blunt distal end 20 to engage the proximal end of the medical device positioned around intermediate portion 19. Blunt distal end 20 is also effective in holding the medical device, for example, a stent or a valve, contained in the device-containing region. This is most effective when the blunt distal end closely approximates the size of catheter lumen 12 of delivery catheter 11.

Distal tip portion 17 of inner member 16 includes tapered proximal end 31, tapered distal end 32 and an intermediate segment 34 disposed between the tapered distal and proximal ends. The tapered distal end facilitates atraumatic placement of the delivery system to the deployment site. Tapered proximal end 31 advantageously provides atraumatic withdrawal of inner member 16 through the valve slit or opening after the medical device has been deployed at the desired vessel site. Intermediate segment 34 approximates the size and shape of catheter lumen 12 of delivery catheter 11 so as to provide an atraumatic transition between the assembled inner member and delivery catheter.

Figure 6:
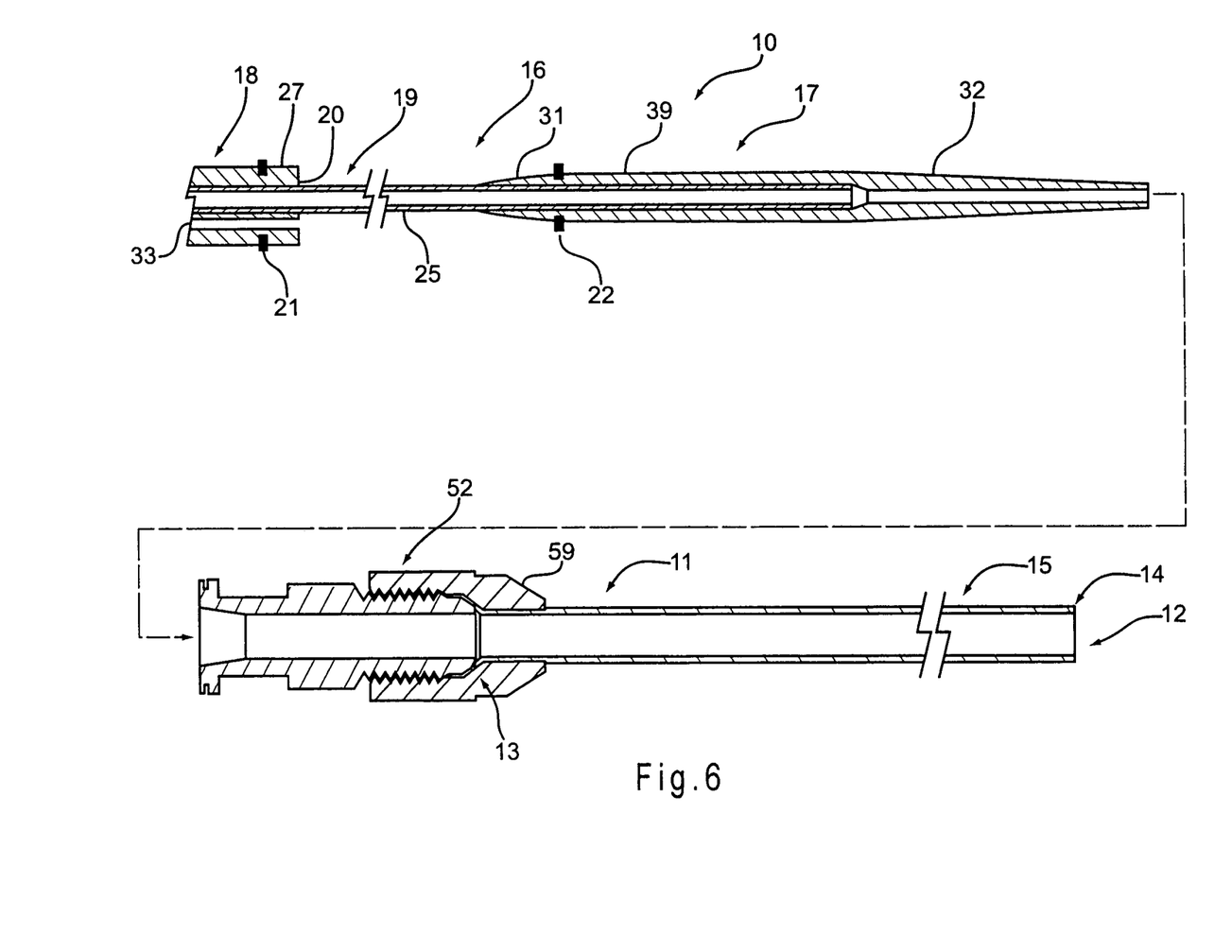
FIG. 6 depicts an enlarged and longitudinally sectioned view of portions of one embodiment of a delivery system of the invention.

FIG. 6 depicts an enlarged and longitudinally sectioned view of one embodiment of a delivery system 10 having an inner member 16 positioned within catheter lumen 12 of delivery catheter 11. Inner member 16 includes inner tube 25 of a radiolucent material such as, for example, well-known medical grade nylon 12 polyamide material. By way of example, inner tube 25 is approximately 77 cm in length with an outside diameter of approximately 0.059 inches, an inside diameter of approximately 0.040 inches, and a wall thickness of approximately 0.0095 inches. This inner tube extends almost the entire length of the inner member through proximal portion 18, intermediate portion 19 and distal tip portion 17. The translucent material of the inner tube through intermediate portion 19 of inner member 16 advantageously provides better fluoroscopic visualization of the medical device contained therearound. For example, the radiolucent material provides very little, if any, interference with the heavier density material or radiopaque markers present in the medical device contained on intermediate portion 19.

Inner member 16 also includes outer tube 27 coaxially positioned around proximal portion of inner tube 25. The outer tube 27 may designate the proximal and distal ends of proximal portion 18 of inner member 16. Outer tube 27 contains delivery lumen 33. First sealing member 21 is positioned on outer tube 27. By way of example, outer tube 27 is approximately 70 cm in length with an outside diameter of approximately 0.117 inches, an inside diameter of approximately 0.062 inches, and a wall thickness of approximately 0.0275 inches of a radiopaque material such as well-known nylon 12 polyamide material filled with a high density radiopaque filler material such as tungsten, barium, bismuth, and the like.

Distal tip section 17 of inner member 16 includes tapered proximal end 31, tapered distal end 32 and intermediate segment 39 disposed therebetween. Second sealing member 22 is positioned on either tapered distal end 32 or intermediate segment 39. By way of example, the distal tip section is preferably 4.5 cm in length with an outside diameter of approximately 0.117 inches, which is approximately the same as the outside diameter of outer tube 27. The distal tip portion 17 can range in length from approximately 1.25 cm to 7 cm. By way of further example, tapered proximal end 31 can range in length from approximately 2.5 mm through 10.0 mm with a preferred length of approximately 5.0 mm. If the tapered proximal end 31 is too short, there may be difficulty in retracting the distal tip section 17 through the valve orifice or slit. In addition, there can be possible induced migration of the valve along with possible damage to the valve itself. Should the tapered proximal end be too long, there is the possibility of wedging the valve between the distal tip section 17 and delivery catheter 11. A taper that is too long may also lead to difficulties with deployment of the stent valve.

Straight intermediate segment 39 can range from approximately 0.0 cm through 3.0 cm with a preferred length of approximately 2.0 cm. Tapered distal end 32 can range in length from approximately 1.0 through 3.0 cm with a preferred length of 2.0 cm. As depicted, the distal end of inner tube 25 extends through tapered proximal end 31 and into straight intermediate segment 39. By way of example, the diameter of the passageway through these segments is approximately 0.059 inches approximating the outside diameter of inner tube 25. A well-known medical grade adhesive is applied to the outside surface of inner tube 25 about the distal end thereof to fixedly attach the inner tube 25 to the distal end portion 32. The remaining portion of the lumen extending through the distal tip portion is approximately 0.038 inches to accommodate a 0.38 inch wire guide. Distal tip portion 17 is formed from a well-known radiopaque nylon 12 polyamide material such as described for outer tube 27.

Delivery catheter 11 comprises, for example, a 9.0 French cylindrical tube of radiopaque fluorinated ethylene propylene (FEP) approximately 60 cm in length with an outside diameter of approximately 0.141 inches, an inside diameter of approximately 0.121 inches, and a wall thickness of approximately 0.010 inches. Luer-lock connector hub 52 comprises well-known threaded female and male connector parts 59 and 60, which are affixidly attached to flared proximal end 13 of delivery catheter 11. Device-containing region 15 of the delivery catheter is adjacent distal end 14 of the delivery catheter through which catheter lumen 12 extends longitudinally therethrough.

In another embodiment, distal tip section 17 includes a radiopaque marker band positioned at the proximal end of intermediate segment 39. The distal end of the marker band is counterbored to engage a recessed flange at the proximal end of the intermediate segment 39. The marker band is disposed next to the intermediate segment 39 over inner tube 25 and held in position with, for example, a medical-grade adhesive or glue such as a commercially available ultraviolet curable glue like Loctite 3311 glue. This glue can be shaped to form tapered proximal end 31. Alternatively, tapered proximal end 31 can be made part of and/or formed with radiopaque marker band 36. As a result, the radiopaque marker band is radiographically visualized so that delivery catheter 11 and distal tip portion 17 of inner member 16 can be visualized during the separation or joining thereof during the delivery process.

In yet other embodiments, intermediate portion 19 of inner member includes radiolucent material to further improve the fluoroscopic visualization of the medical device. Inner lumen 24 extending longitudinally through the delivery device and, in particular, inner member 16 is used for guiding the delivery system over a well-known guide wire to the deployment site in the vascular system of the patient. Such a guide wire extends through inner lumen 24. Delivery catheter 11 can also contain portions manufactured from radiolucent material to improve visualization of the medical device. Further examples of inner members and delivery catheters having radiolucent and radiopaque materials positioned to assist in the deployment of a medical device from the delivery system are disclosed in U.S. Publication No. 2003/0144670, published Jul. 31, 2003, the contents of which are incorporated by reference.

Figure 7:
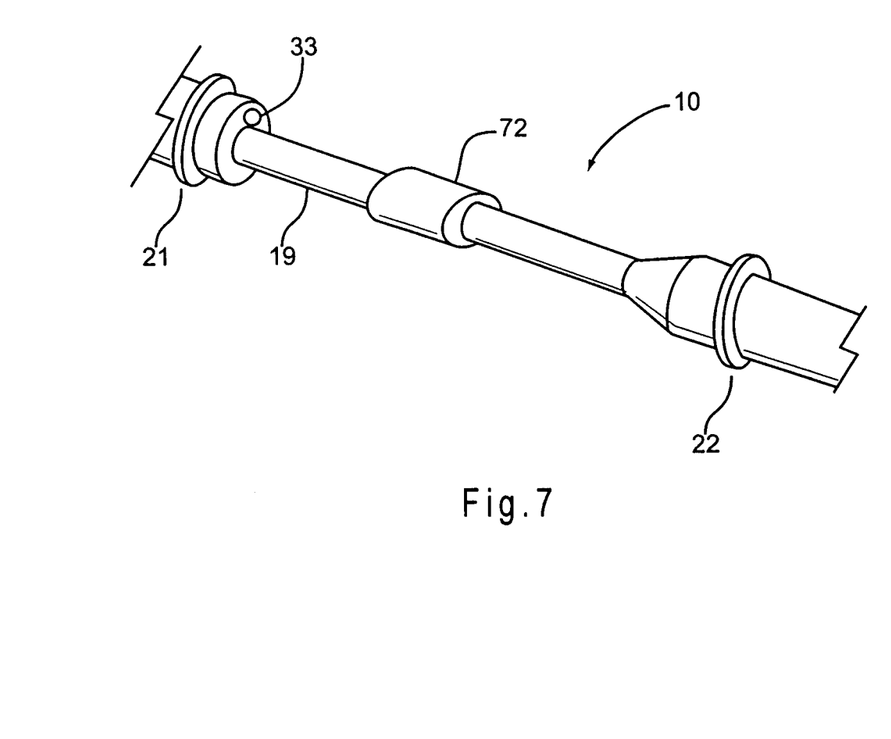
FIG. 7 depicts one embodiment of the intermediate portion of the inner member of a delivery system of the invention.

In certain embodiments, intermediate portion 19 of inner member 16 is shaped to hold a medial device at a preferred orientation. FIG. 7 shows one such embodiment having elliptical member 72 positioned on intermediate portion 19 within the device-containing region. Of course, shapes other than elliptical may be used to hold the medical device in a preferred orientation.

It is to be understood that the above-described delivery systems are merely illustrative embodiments of the principles of this invention and that other delivery systems may be devised by those skilled in the art without departing from the spirit and scope of this invention. In particular, the distal end of the proximal portion of the inner member may be configured to engage the proximal end of the medical device positioned in the intermediate portion of the inner member. Furthermore, the proximal end of the distal tip portion of the inner member can be configured in any number of different ways to receive and engage the distal end of the medical device. These configurations are used to engage and rotate the medical device while still being able to determine the orientation of the medical device from the proximal end of the delivery system typically positioned outside of the patient during a percutaneous delivery procedure.

Delivery Methods

Another aspect of the invention provides methods of delivering an implantable medical device to a body vessel. The devices and methods of the invention are desirably adapted for the deployment of the device within the human or veterinary vasculature. However, such devices and methods may be adapted for deployment of a medical device within any tube-shaped body passage lumen, including but not limited to the biliary ducts, ureteral passages or alimentary canal.

This method has particular advantages for the delivery of an expandable medical device requiring or benefiting from maintenance of the hydration of at least part of the device. Such implantable devices include, but are not limited to, venous valves including a natural tissue or artificial leaflet material, grafts, vena cava filters and stent grafts.

In one embodiment, the method includes providing one of the embodiments of the delivery system disclosed above having a side port positioned distally of the second sealing member. The expandable medical device is contained within the device-containing region. This region is positioned at a delivery position within the body vessel using a percutaneous entry technique well known to those skilled in the art. For example, the method may include delivering the distal portion of a guide wire to the delivery site and positioning the proximal end of the guide wire within the inner lumen at the distal end of the inner member. The device-containing region can then be delivered via a path defined by the guide wire.

The device-containing region is positioned beyond (distally of) the distal end of the delivery catheter. This is achieved by either moving the inner member distally or moving the delivery catheter proximally. The expandable medical device is then deployed. In one embodiment, the device is self-expandable. For example, the device may contain a self-expandable nickel titanium alloy, such as NITINOL or a similar material. Alternatively, the self-expandable medical device may include a frame having at least one spring-like portion that expands upon retraction of the delivery catheter. After the device is deployed, the delivery system is withdrawn from the body vessel.

In one embodiment, the method also includes flushing a hydrating fluid from the device-containing region prior to positioning the intermediate portion within the body vessel. Such a process has particular application in situations where the medical device is stored in the device-containing region in the presence of a hydrating fluid. This process allows for the hydrating fluid to be flushed from the device-containing region prior to deployment. In certain embodiments, the hydration fluid may be replaced by a different hydration fluid, or even a fresh batch of the same hydration fluid.

The hydrating fluid is flushed by positioning the side port(s) proximally of the second sealing member and distally of the first sealing member. In this position, the side port(s) provide a fluid communication path between the device-containing region and the exterior of the delivery catheter. A flushing fluid is delivered to the device-containing region via the lateral port and a delivery lumen, such as delivery lumen 33. Delivery of the flushing fluid expels at least a portion of the hydrating fluid though the side port.

Kits Including a Delivery System and an Implantable Medical Device

Kits including the delivery system and an implantable medical device positioned within the device-containing region of the delivery system are also provided. On one embodiment, a device-containing region also includes a hydration fluid in contact with at least a portion of the implantable medical device. The kit can also include sterile packaging material and/or instruction material. Such kits may include more than one delivery system, each containing an implantable medical device. The implantable medical devices can be of substantially the same size and shape, or, alternatively, can vary with respect to size and shape so as to accommodate placement in body vessels of differing sizes. In such embodiments, the kit may further include visible indicia identifying the implantable medical device as, for example, a venous or other vascular valve of a particular size, and/or can contain or otherwise be associated with printed materials identifying the implantable medical device as a venous or other vascular valve and including information concerning its use.

The present invention is useful for placement of a medical device within a human or veterinary patient, and therefore finds applicability in human and veterinary medicine. It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

The scope of the invention is defined by the appended claims, and all devices and methods that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A delivery system comprising:
   a delivery catheter having an catheter lumen extending from a proximal end of the delivery catheter to a distal end of the delivery catheter;
   an inner member extending through the catheter lumen, the inner member comprising a distal tip portion, a proximal portion, an intermediate portion and an inner lumen extending longitudinally therethrough from a proximal end of the inner member to a distal end of the inner member, wherein the intermediate portion is disposed adjacent to the distal end of the delivery catheter;
   a first sealing member positioned between the inner member and the delivery catheter, wherein the first sealing member forms a fluid seal between the inner member and an inside surface of the delivery catheter;
   a second sealing member positioned distally from the first sealing member between the inner member and the delivery catheter, wherein the second sealing member forms a fluid seal between the inner member and an inside surface of the delivery catheter;
   wherein the intermediate portion is at least that portion extending between the first sealing member and the second sealing member;

a device-containing region between the intermediate portion and the delivery catheter, wherein the device-containing region is defined by the first sealing member and the second sealing member a delivery lumen extending longitudinally through the inner member from near a proximal end of the inner member and being in fluid communication with the device-containing region;

a side port in the delivery catheter providing fluid communication between the device-containing region and an outside of the delivery catheter when the side port is positioned proximally of the second sealing member and distally of the first sealing member; and wherein the delivery catheter is movable relative to the inner member to position the side port distally of the second sealing member thereby the side port does not provide fluid communication between the device-containing region and the outside of the delivery catheter, the device-containing region thereby being entirely sealed from the outside of the delivery catheter.

2. The delivery system of claim 1, wherein the intermediate portion is sized and shaped to engage a medical device between the inner member and the delivery catheter.

3. The delivery system of claim 2, wherein the implantable medical device is an expandable medical device requiring or benefiting from maintenance of hydration of at least part of the implantable medical device.

4. The delivery system of claim 1, further comprising an implantable medical device positioned within the device-containing region.

5. The delivery system of claim 1, further comprising a hydrating fluid contained within the device-containing region.

6. The delivery system of claim 1, wherein at least one of the first sealing member and the second sealing member is a ring seal.

7. The delivery system of claim 6, wherein at least one of the first sealing member and the second sealing member is an O ring seal.

8. The delivery system of claim 1, wherein the inner member comprises a radiolucent material.

9. The delivery system of claim 1, wherein the delivery catheter comprises a radiopaque material.

10. A kit comprising the delivery system of the claim 1, further comprising an implantable medical device positioned in the device-containing region of the delivery system and a hydration fluid contained in the device-containing region and in contact with at least a portion of the medical device.

11. The kit of claim 10, wherein the first sealing member and the second sealing member attach to the inner member.

12. The delivery system of claim 1, where the fluid seal formed by the first sealing member and by the second sealing member is sufficient to maintain a hydrating environment within the device-containing region.

13. The delivery system of claim 1, wherein the first sealing member and the second sealing member attach to the inner member.

14. A delivery system comprising:
    a delivery catheter having a catheter lumen extending from a proximal end of the delivery catheter to a distal end of the delivery catheter;
    an inner member extending through the catheter lumen, the inner member comprising a distal tip portion, a proximal portion, an intermediate portion and a delivery lumen extending longitudinally therethrough from near a proximal end of the inner member to a device-containing region positioned between the intermediate portion and the delivery catheter, wherein the intermediate portion is disposed adjacent to the distal end of the delivery catheter;
    a first sealing member positioned between the inner member and the delivery catheter, wherein the first sealing member forms a fluid seal between the inner member and an inside surface of the delivery catheter;
    a second sealing member positioned distally from the first sealing member between the inner member and the delivery catheter, wherein the second sealing member forms a fluid seal between the inner member and an inside surface of the delivery catheter, wherein the intermediate portion is that portion extending between the first seal and the second seal;
    a lateral port in fluid communication with a proximal end of the delivery lumen;
    a side port in the delivery catheter providing fluid communication between the device-containing region and an outside of the delivery catheter when the side port is positioned proximally of the second sealing member and distally of the first sealing member;
    a hydrating fluid contained within the device-containing region;
    an implantable medical device positioned within the device-containing region, wherein at least a portion of the implantable medical device contacts the hydrating fluid; and
    wherein the delivery catheter is movable relative to the inner member to position the side port distally of the second sealing member thereby the side port does not provide fluid communication between the device-containing region and the outside of the delivery catheter, the device-containing region thereby being entirely sealed from the outside of the delivery catheter.

15. The delivery system of claim 14, wherein the first sealing member and the second sealing member attach to the inner member.

* * * * *

UNITED STATES PATENT AND TRADEMARK OFFICE
CERTIFICATE OF CORRECTION

| | | |
|---|---|---|
| PATENT NO. | : 8,814,847 B2 | Page 1 of 1 |
| APPLICATION NO. | : 11/827848 | |
| DATED | : August 26, 2014 | |
| INVENTOR(S) | : Hoffman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1336 days.

Signed and Sealed this
Fifteenth Day of September, 2015

Michelle K. Lee
*Director of the United States Patent and Trademark Office*